(12) United States Patent
Davis

(10) Patent No.: US 10,322,055 B1
(45) Date of Patent: Jun. 18, 2019

(54) LEG ATTACHED MEDICAL DOLLY SYSTEM

(71) Applicant: Johna Davis, Chandler, AZ (US)

(72) Inventor: Johna Davis, Chandler, AZ (US)

( * ) Notice: Subject to any disclaimer, the term of this patent is extended or adjusted under 35 U.S.C. 154(b) by 0 days.

(21) Appl. No.: 16/032,154

(22) Filed: Jul. 11, 2018

(51) Int. Cl.
*A61G 7/10* (2006.01)
*A61M 5/14* (2006.01)
*A61H 3/04* (2006.01)

(52) U.S. Cl.
CPC ............ *A61H 3/04* (2013.01); *A61G 7/1046* (2013.01); *A61M 5/1415* (2013.01); *A61M 5/1417* (2013.01); *A61M 2005/1416* (2013.01)

(58) Field of Classification Search
CPC ..... A61H 3/04; A61G 7/1046; A61M 5/1415; A61M 5/1417; A61M 2005/1416
See application file for complete search history.

(56) References Cited

U.S. PATENT DOCUMENTS

| | | | | |
|---|---|---|---|---|
| 2,723,665 A | * | 11/1955 | Goldsmith | A61M 5/1415 128/877 |
| 2,917,769 A | * | 12/1959 | Kasper | A47L 9/009 15/246.4 |
| 3,802,717 A | * | 4/1974 | Eitreim | B62B 5/0083 248/154 |
| 4,222,580 A | * | 9/1980 | Krokonko | B62B 3/104 248/98 |
| 4,295,293 A | | 10/1981 | Baclit | |
| D270,962 S | | 10/1983 | Martell | |
| 4,526,187 A | * | 7/1985 | Ciullo | A61H 3/02 128/DIG. 6 |
| 5,479,953 A | | 1/1996 | Pasulka | |
| 5,551,105 A | | 9/1996 | Short | |
| 6,056,249 A | | 5/2000 | Fillon, Jr. | |
| 6,708,991 B1 | | 3/2004 | Ortlieb | |
| 8,662,458 B2 | | 3/2014 | Henault | |
| 10,046,108 B2 | * | 8/2018 | Nesler | A61M 5/1415 |

FOREIGN PATENT DOCUMENTS

WO  WO2007056830  5/2007

\* cited by examiner

*Primary Examiner* — Anita M King

(57) ABSTRACT

A leg attached medical dolly system for increasing user mobility while attached to a medical device includes a base platform having an upper surface, a lower surface, an outer edge, and an aperture. An equipment strap has a first segment and a second segment attached to the base platform. The first segment has a first equipment closure mechanism that is selectively engageable with a second equipment closure mechanism of the second segment to secure a medical device to the base platform. A plurality of wheels is coupled to the lower surface of the base platform. A tether has a platform end attached to the base platform through the aperture and a harness end with a harness attachment mechanism. A harness assembly is wearable by a user, and the harness attachment mechanism attaches to the harness assembly such that the base platform is pulled by the tether as the user moves.

10 Claims, 5 Drawing Sheets

LEG ATTACHED MEDICAL DOLLY SYSTEM

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION (1) Field of the Invention (2) Description of Related Art Including Information Disclosed Under 37 CFR 1.97 and 1.98

The disclosure and prior art relates to medical dollies and more particularly pertains to a new medical dolly system for increasing user mobility while attached to a medical device.

BRIEF SUMMARY OF THE INVENTION

An embodiment of the disclosure meets the needs presented above by generally comprising a base platform having an upper surface, a lower surface, an outer edge, and an aperture extending through from the upper surface to the lower surface and proximal the outer edge. An equipment strap has a first segment with a first equipment closure mechanism and a second segment with a second equipment closure mechanism. Each of the first segment and the second segment is attached to the lower surface of the base platform proximal the outer edge. The first equipment closure mechanism is selectively engageable with the second equipment closure mechanism to secure a medical device to the upper surface of the base platform. A plurality of wheels is coupled to the lower surface of the base platform. A tether has a platform end and a harness end. The platform end is attached to the base platform through the aperture and the harness end has a harness attachment mechanism. A harness assembly is wearable by a user, wherein the harness attachment mechanism selectively attaches to the harness assembly such that the base platform is pulled by the tether as the user moves.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
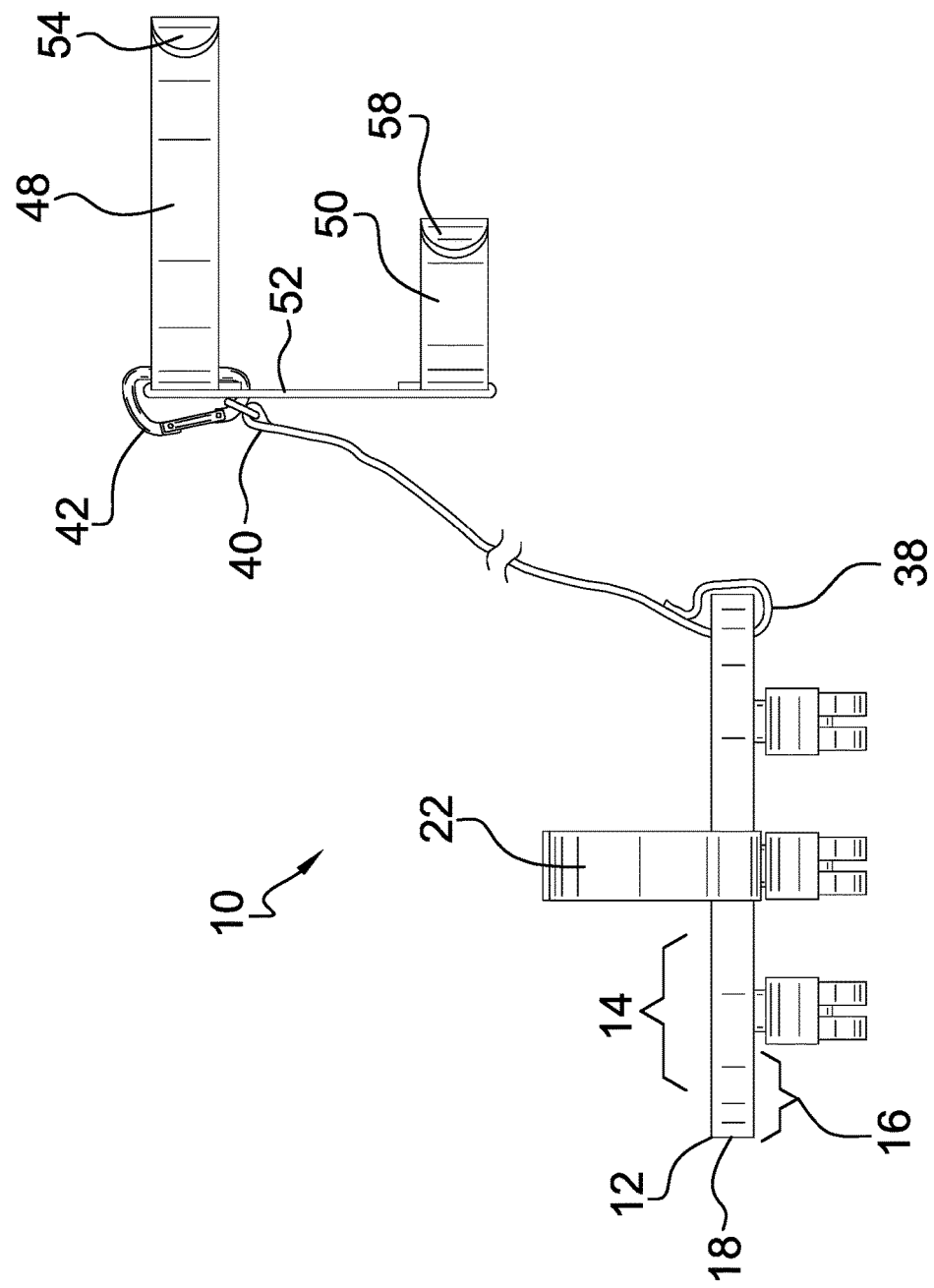
FIG. 1 is a front elevation view of a leg attached medical dolly system according to an embodiment of the disclosure.
Figure 2:
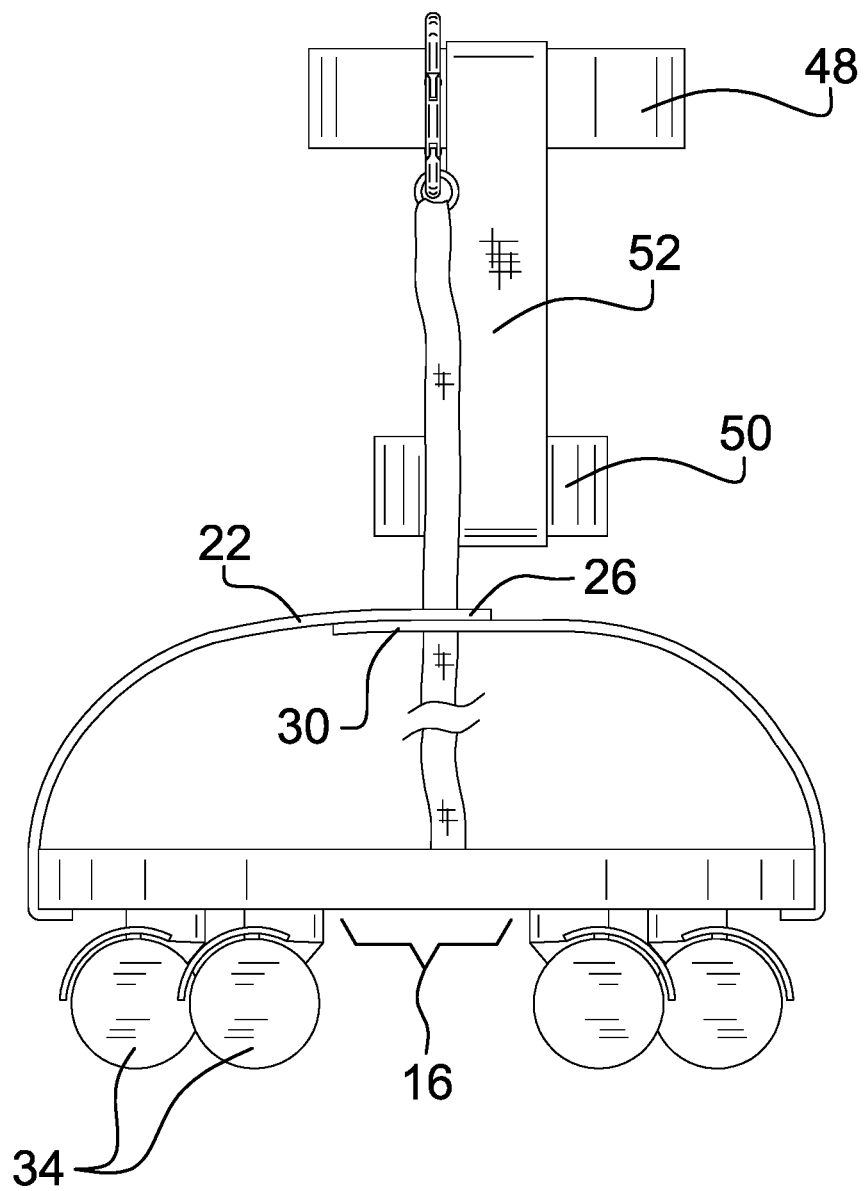
FIG. 2 is a side elevation view of an embodiment of the disclosure.
Figure 3:
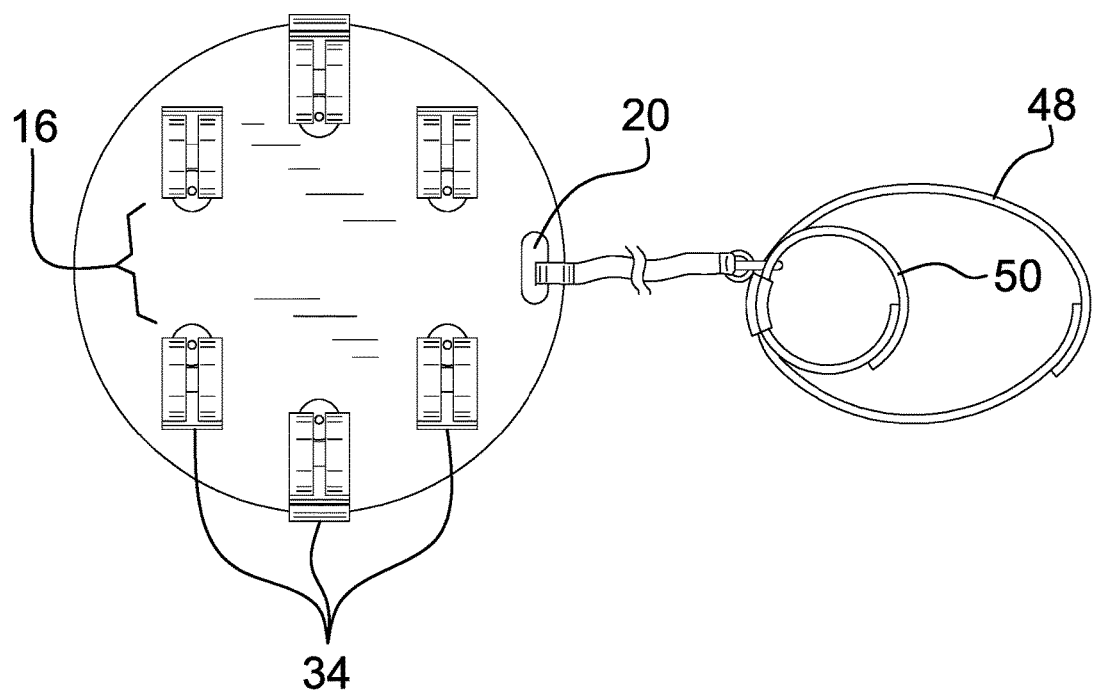
FIG. 3 is a bottom plan view of an embodiment of the disclosure.
Figure 4:
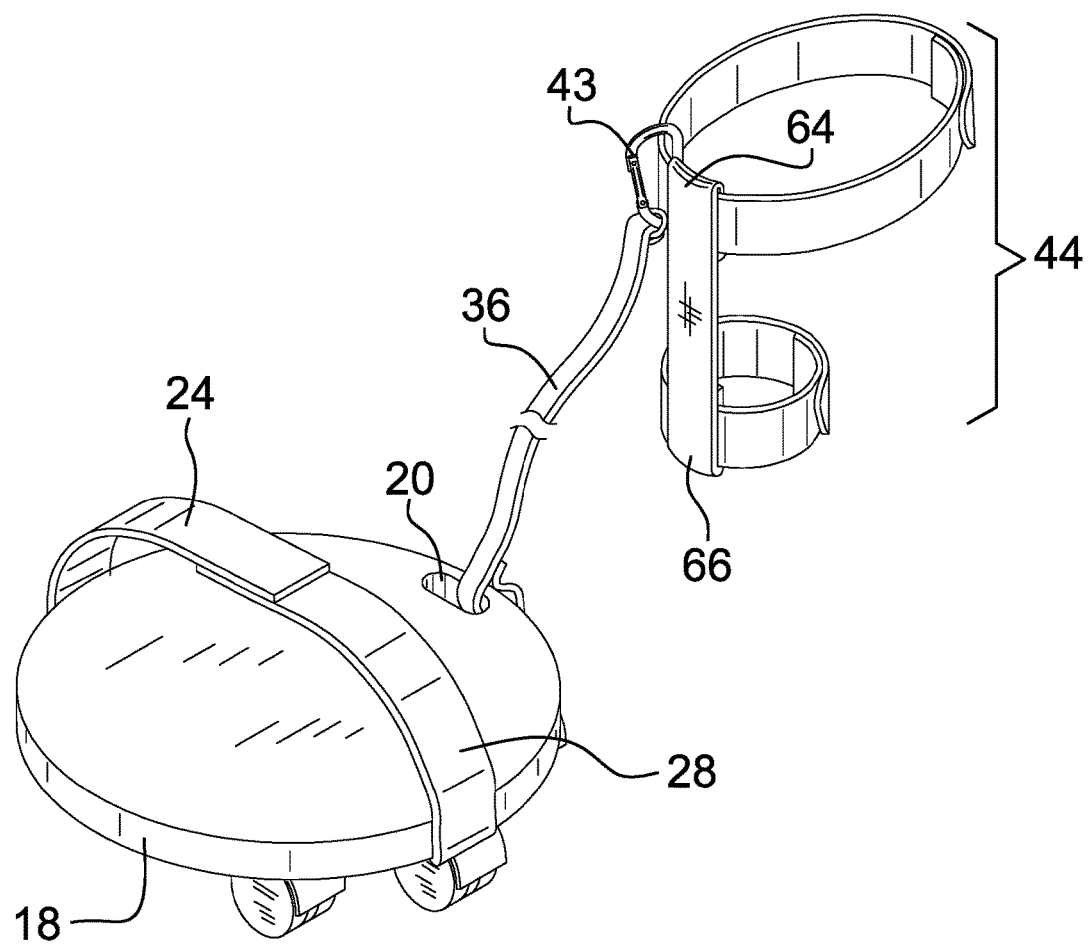
FIG. 4 is an isometric view of an embodiment of the disclosure.
Figure 5:
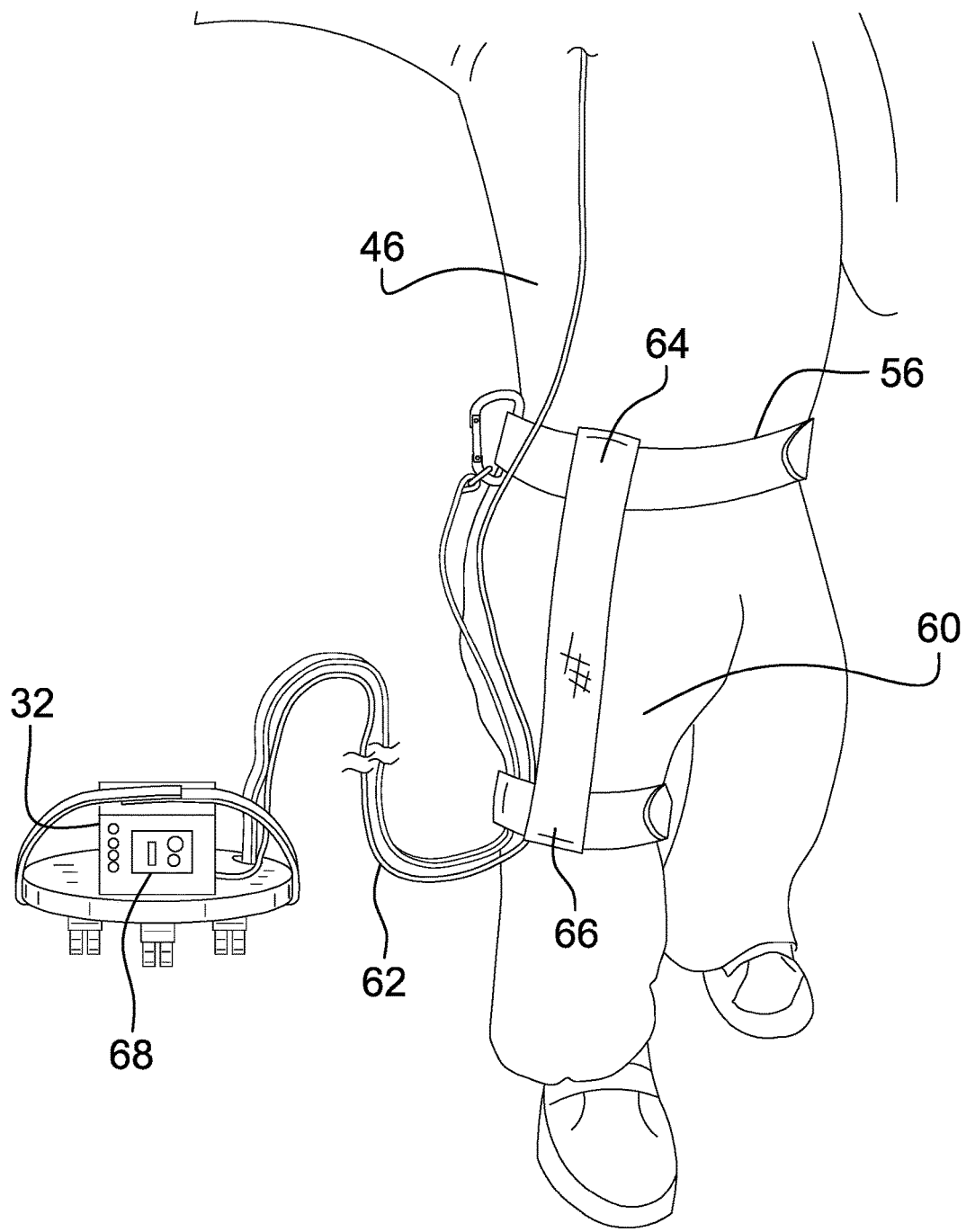
FIG. 5 is an in-use view of an embodiment of the disclosure.

With reference now to the drawings, and in particular to FIGS. 1 through 5 thereof, a new medical dolly embodying the principles and concepts of an embodiment of the disclosure and generally designated by the reference numeral 10 will be described.

As best illustrated in FIGS. 1 through 5, the leg attached medical dolly system 10 generally comprises a base platform 12 having an upper surface 14, a lower surface 16, an outer edge 18, and an aperture 20 extending through from the upper surface 14 to the lower surface 16 and proximal the outer edge 18. The base platform may be circular in order to minimize contact with objects and to eliminate corners in case it hits a person. An equipment strap 22 has a first segment 24 with a first equipment closure mechanism 26 and a second segment 28 with a second equipment closure mechanism 30. Each of the first segment 24 and the second segment 28 is attached to the lower surface 16 of the base platform 12 proximal the outer edge 18. The first equipment closure mechanism 26 is selectively engageable with the second equipment closure mechanism 30 to secure a medical device 32 to the upper surface 14 of the base platform. A plurality of wheels 34 is coupled to the lower surface 16 of the base platform. The plurality of wheels may be six wheels. Each of the plurality of wheels may be rotatable, allowing the base platform to spin and move in any direction. A tether 36 has a platform end 38 and a harness end 40. The platform end 38 is attached to the base platform 12 through the aperture 20 and the harness end 40 has a harness attachment mechanism 42. The harness attachment mechanism may be a carabiner 43. A harness assembly 44 is wearable by a user 46, wherein the harness attachment mechanism 42 selectively attaches to the harness assembly 44 such that the base platform 12 is pulled by the tether 36 as the user moves.

The harness assembly 44 may comprise a waist belt 48, a thigh strap 50, and a connection strap 52. The waist belt 48 has a waist belt closure mechanism 54 that is configured to adjustably attach to a waistline 56 of the user. The waist belt 48 is selectively engageable with the harness attachment mechanism 42 of the tether. The thigh strap 50 has a thigh strap closure mechanism 58 that is configured to adjustably attach to a lower thigh 60 of the user. The thigh strap 50 is configured to secure the tether 36 and a tube 62 of the medical device 32. The connection strap 52 has an upper end 64 attached to the waist belt 48 and a lower end 66 attached to the thigh strap. Each of the first equipment closure mechanism 26, the second equipment closure mechanism 30, the waist belt closure mechanism 54, and the thigh strap closure mechanism 58 may be a hook-and-loop fastener.

In use, the user places the medical device such as a feeding pump 68 onto the base platform 12 and secures the feeding pump with the equipment strap 22. The user wears the harness assembly 44 and attaches the tether 36 the waist belt 48. The user passes the tether and the tube 62 of the feeding pump through the thigh strap 50 in order to prevent them from being tugged. The user can then walk freely with the feeding pump 68 traveling behind on the base platform 12.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A leg attached medical dolly system, the system comprising:
    a base platform having an upper surface, a lower surface, an outer edge, and an aperture extending through from the upper surface to the lower surface and proximal the outer edge;
    an equipment strap having a first segment and a second segment, the first segment having a first equipment closure mechanism and the second segment having a second equipment closure mechanism, each of the first segment and the second segment being attached to the lower surface of the base platform proximal the outer edge, the first equipment closure mechanism being selectively engageable with the second equipment closure mechanism, wherein the equipment strap is configured to secure a medical device to the upper surface of the base platform;
    a plurality of wheels coupled to the lower surface of the base platform;
    a tether having a platform end and a harness end, the platform end being attached to the base platform through the aperture, the harness end having a harness attachment mechanism; and
    a harness assembly, wherein the harness assembly is configured to be worn by a user, wherein the harness attachment mechanism is configured to selectively attach to the harness assembly such that the base platform is pulled by the tether as the user moves.

2. The leg attached medical dolly system of claim 1, wherein the harness assembly further comprises a waist belt having a waist belt closure mechanism, the waist belt closure mechanism being adjustably attachable to a waistline of the user, the waist belt being selectively engageable with the harness attachment mechanism of the tether.

3. The leg attached medical dolly system of claim 2, wherein the harness assembly further comprises:
    a thigh strap having a thigh strap closure mechanism, the thigh strap closure mechanism being adjustably attachable to a lower thigh of the user, wherein the thigh strap is configured to secure the tether and a tube of the medical device; and
    a connection strap having an upper end and a lower end, the upper end being attached to the waist belt and the lower end being attached to the thigh strap.

4. The leg attached medical dolly system of claim 3 wherein the base platform is circular.

5. The leg attached medical dolly system of claim 2 wherein each of the first equipment closure mechanism, the second equipment closure mechanism, and the waist belt closure mechanism is a hook-and-loop fastener.

6. The leg attached medical dolly system of claim 3 wherein each of the first equipment closure mechanism, the second equipment closure mechanism, the waist belt closure mechanism, and the thigh strap closure mechanism is a hook-and-loop fastener.

7. The leg attached medical dolly system of claim 3 wherein the harness attachment mechanism is a carabiner.

8. The leg attached medical dolly system of claim 6 wherein the plurality of wheels is six.

9. The leg attached medical dolly system of claim 6 wherein each of the plurality of wheels is rotatable.

10. A leg attached medical dolly system, the system comprising:
    a circular base platform having an upper surface, a lower surface, an outer edge, and an aperture extending through from the upper surface to the lower surface and proximal the outer edge;
    an equipment strap having a first segment and a second segment, the first segment having a first equipment closure mechanism and the second segment having a second equipment closure mechanism, each of the first segment and the second segment being attached to the lower surface of the base platform proximal the outer edge, the first equipment closure mechanism being selectively engageable with the second equipment closure mechanism, wherein the equipment strap is configured to secure a medical device to the upper surface of the base platform;
    a plurality of wheels coupled to the lower surface of the base platform, wherein the plurality of wheels is six, wherein each of the plurality of wheels is rotatable;
    a tether having a platform end and a harness end, the platform end being attached to the base platform through the aperture, the harness end having a harness attachment mechanism, the harness attachment mechanism being a carabiner;

a harness assembly, the harness assembly comprising
- a waist belt having a waist belt closure mechanism, wherein the waist belt closure mechanism is configured to be adjustably attachable to a waistline of the user, the waist belt being selectively engageable with the harness attachment mechanism of the tether,
- a thigh strap having a thigh strap closure mechanism, wherein the thigh strap closure mechanism is configured to be adjustably attachable to a lower thigh of the user, wherein the thigh strap is configured to secure the tether and a tube of the medical device, and
- a connection strap having an upper end and a lower end, the upper end being attached to the waist belt and the lower end being attached to the thigh strap,
- wherein the harness assembly is configured to be worn by a user, wherein the harness attachment mechanism is configured to selectively attach to the waist belt such that the base platform is pulled by the tether as the user moves;

wherein each of the first equipment closure mechanism, the second equipment closure mechanism, the waist belt closure mechanism, and the thigh strap closure mechanism is a hook-and-loop fastener.

* * * * *